United States Patent [19]

Bogie

[11] Patent Number: 4,459,217

[45] Date of Patent: Jul. 10, 1984

[54] DENTURE CLEANSING COMPOSITIONS

[75] Inventor: David K. Bogie, Pretoria, South Africa

[73] Assignee: Reckitt & Colman Products Limited, London, England

[21] Appl. No.: 304,158

[22] Filed: Sep. 21, 1981

Related U.S. Application Data

[63] Continuation-in-part of Ser. No. 285,830, Jul. 22, 1981, abandoned, which is a continuation of Ser. No. 81,802, Oct. 4, 1979, abandoned.

[51] Int. Cl.$^3$ .................. C11D 7/18; C11D 7/38; C11D 7/56
[52] U.S. Cl. .................. 252/174.14; 252/99; 252/136; 252/142; 252/186.1; 252/550; 252/DIG. 4; 252/DIG. 16; 252/174
[58] Field of Search .......... 252/DIG. 4, DIG. 16, 252/99, 136, 142, 174.14, 174.18, 174.24, 186.1, 550, 174

[56] References Cited

FOREIGN PATENT DOCUMENTS 0264015 8/1968 Austria .

*Primary Examiner*—John E. Kittle
*Assistant Examiner*—Hoa Van Le
*Attorney, Agent, or Firm*—Bacon & Thomas

[57] ABSTRACT

An anhydrous denture cleansing composition, having a free surface moisture content of less than 0.5% for dissolution in water to form a denture cleansing bath, consisting essentially of 10% to 40% by weight of a permonosulphate of the formula $M^1HSO_5$ wherein $M^1$ is an alkali metal cation; a tartar removal component selected from the group consisting of succinic acid, malic acid, tartaric acid, citric acid, a bisulphate of the formula $M^2HSO_4$ wherein $M^2$ is an alkali metal cation, and mixtures thereof; and an amount of a substantially chloride-free anhydrous alkali metal carbonate of formula $M^3_2CO_3$ wherein $M^3$ is an alkali metal cation which amount is sufficient to develop an initial pH of $\leq 4.5$ in the denture cleansing bath.

23 Claims, No Drawings

DENTURE CLEANSING COMPOSITIONS

This application is a continuation-in-part of application Ser. No. 06/285,830, filed July 22, 1981, now abandoned, which is a continuation of application Ser. No. 06/081,802, filed Oct. 4, 1979, now abandoned.

BACKGROUND OF THE INVENTION

1. Field of Invention

This invention relates to denture cleansing compositions and to processes for making such compositions.

2. Description of the Prior Art

Denture cleansing compositions are known and generally comprise solids compositions which produce a more or less strongly alkaline reaction on dissolution in water to form a cleansing bath. Tablets have been found to be an acceptable form of presentation for such denture cleansers, facilitating dosage control both in manufacture and use, improving ease of handling from a package point of view, and in storage. Such tabletted compositions clean dentures but do not completely remove accumulations of calculus or tartar.

Known acid-reacting compositions, such as those containing hydrochloric acid, remove calculus or tartar but such compositions cannot be tabletted, require special handling and packaging and are inconvenient in use so that their application to denture cleansing compositions generates many problems in both manufacture and use. Thus, no strongly acid-reacting denture cleansing tablets have yet been successfully marketed.

Austrian Patent Specification No. 264015 suggests the preparation of mixtures capable of dissolving in water to form a cleansing solution having an initial pH $\leq 5$, preferably pH 1.5–4.5 and containing inter alia monopotassium permonosulphate, a carbonate of sodium and an acid reacting substance including sodium bisulphate or a fruit acid. Further it is proposed that certain of such mixtures be formed into tablets for dissolution in water to form a denture cleansing bath and suggested that the tables may dissolve within 7 minutes.

The disclosure in Austrian Patent Specification No. 264015 does not however suggest how the mixtures are to be handled and, more particularly, how the tablets are to be made on a commercial scale. Indeed the moisture content of the suggested components produce mixtures and tablets which are not storage stable and the tablets take an inordinately long time to dissolve. Further, whilst tablets may be successfully produced by hand in accordance with the prior disclosure such processing is not commercially viable and does not produce a fast-dissolving tablet which can effectively remove calculus and generally clean dentures within ten minutes, a period to which the public has now become accustomed.

SUMMARY OF THE INVENTION

An object of the present invention is to produce a novel denture cleansing composition having a pH of $\leq 4.5$.

A further object of the present invention is to produce a denture cleansing composition capable of being tabletted at the high speeds necessary for commercial production.

A further object of the present invention is to produce a tablet capable of dissolving in an aliquot of water to produce a denture cleansing bath having a pH of $\leq 4.5$.

A further object of the invention is to produce a tablet capable of dissolving in an aliquot of water in less that 5 minutes to produce a denture cleansing bath initially having a pH of $\leq 4.5$ A still further object of the invention is to provide a novel process for making the composition of the present invention.

STATEMENT OF THE INVENTION

According to the present invention there is provided an anhydrous denture cleansing composition having a free surface moisture content less than 0.5%, for dissolution in water to form a denture cleansing bath, consisting essentially of 10% to 40% by weight of a permonosulphate of formula $M^1HSO_5$ wherein $M^1$ is an alkali metal cation, a tartar removal component selected from the group consisting of succinic acid, malic acid, tartaric acid, citric acid, a bisulphate of formula $M^2HSO_4$ wherein $M^2$ is an alkali metal cation, and mixtures thereof, and an amount of a substantially chloride-free anhydrous alkali metal carbonate of formula $M_2^3CO_3$ wherein $M^3$ is an alkali metal cation, which amount is sufficient to develop an initial pH of $\leq 4.5$ in the denture cleansing bath.

Preferably $M^1$ is potassium, $M^2$ is sodium or potassium or a mixture thereof, and $M^3$ is sodium. Conveniently the composition may include up to 50% of an alkali metal bicarbonate, by weight based on the alkali metal carbonate.

In one embodiment of the invention when the tartar removal component comprises an alkali metal bisulphate $M^2HSO_4$, the free surface moisture content of the composition is less than 0.2% by weight of the composition.

Preferably the tartar removal component comprises up to 45% by weight of the composition, conveniently from 2% to 40% by weight of the composition and most preferably from 17% to 28% by weight of the composition.

In a preferred embodiment of the invention $M^1$ is potassium, $M^2$ is potassium and sodium, and the permonosulphate is present as the triple salt $KHSO_4.K_2SO_4.2KHSO_5$.

Preferably at least part of the tartar removal component comprises tartaric acid and conveniently the amount of chloride-free anhydrous alkali metal carbonate is present in a stoichiometrical amount to form with the tartaric acid, sodium hydrogen tartrate when the composition is dissolved in water to form a denture cleansing bath.

The composition may conveniently contain an antirestaining agent which may be present at levels up to 10% by weight of the composition. By anti-restaining agent is meant a compound which inhibits or prevents rapid restaining of prostheses following cleaning thereof by strongly acid reacting compositions such as form the subject of the present invention. The phenomenon of restaining may be due at least in part to staining of prosthesis surfaces etched by tartar and/or the acid cleanser. Alternatively, removal of tartar, achieved solely by acid baths, may result in unusual cleanliness so that any discolouration, by contrast, becomes the more remarkable.

Some anti-restaining agents are acid reacting and may be effective at least in part as tartar removers. For the purposes of the present description the anti-restaining aid forms no part of the tartar removal component notwithstanding its possible tartar removal propensity.

Suitable anti-restaining components are sulphamic acid, the alkali metal phoshates, especially the acid phosphates such as disodium dihydrogen pyrophosphate.

The composition may also conveniently contain dehydrated sodium perborate monohydrate. Dehydrated sodium perborate monohydrate reacts with water to produce effervescent oxygen. This dehydrated sodium perborate acts as a tabletting aid and at least assists in disintegrating tablets containing it by virtue of the liberation of effervescent oxygen in water. The dehydrated sodium perborate monohydrate may be present at from 2.5% to 6.0% by weight of the composition, and in which case it is preferably admixed with anhydrous sodium carbonate and a minor amount of a surfactant such as sodium dodecylbenzene sulphonate.

The composition may also conveniently contain a further disintegrative material, present at from 2% to 20% by weight of the composition, and which may be materials which can be dried to requisite moisture contents and typically comprise a microcrystalline cellulose, or derivative thereof, or a derivative of sodium alginate. Such materials advantageously act also as binding aids during tabletting.

The composition may also conveniently include at least one known colourant, and/or known flavourant, and/or known aid to tabletting each below 0.2% by weight of the composition and most preferably less than 0.1% by weight of the composition.

The invention also envisages a tablet comprising a composition in accordance with the invention, conveniently consisting of a unit dose of the composition and capable of dissolving in an aliquot of water in less than 5 minutes, more preferably in less than 2 minutes.

The invention also envisages a process for the preparation of an anhydrous denture cleansing composition for dissolution in water to form a denture cleansing bath comprising 10% to 40% by weight of at least one permonosulphate of formula $M^1HSO_5$ wherein $M^1$ is an alkali metal cation, a tartar removal component selected from the group consisting of succinic acid, malic acid, tartaric acid, citric acid, a bisulphate of formula $M^2HSO_4$ wherein $M^2$ is an alkali metal cation, and mixtures thereof, and an amount of a substantially chloride-free anhydrous alkali metal carbonate of formula $M_2^3CO_3$ wherein $M^3$ is an alkali metal cation, said chloride-free anhydrous alkali metal carbonate being in sufficient amount to develop an initial pH of $\leq 4.5$ in the denture cleansing bath, comprising the steps of predrying selected components of the composition and dry mixing the dried components with the other components to produce the denture cleansing composition.

Preferably the process includes the additional step of tabletting the composition.

Preferably also the said selected components are the tartar removal component and the anhydrous alkali metal carbonate.

In a preferred process in accordance with the invention components are dried to a free surface moisture content of 0.02% to 0.5% by weight of the composition and, when the tartar removal component includes an alkali metal bisulphate, the selected components are preferably dried to a free surface moisture content $\leq 0.2\%$ w/w.

Preferably the drying step is conducted on a fluid bed drier at 80° C. for fifteen minutes.

The invention also envisages a tablet prepared by the methods according to the invention, more specifically a tablet of such composition as to dissolve in an aliquot of water at a temperature of 20° C. to 50° C. within 5 minutes and more preferably in less than 2 minutes.

In a preferred embodiment in accordance with the invention tablets are prepared by predrying sodium bisulphate and/or fruit acid to a moisture content 0.5% w/w and preferably 0.1–0.2% w/w. A premix is made of the sodium bisulphate and/or fruit acid and flavourant and colourant used. The balance of components is dry-mixed in any order with the pre-mix in a suitable mixer. The mixture is then tabletted in known manner.

The tablets according to the invention have been found to be storage-stable and even after long storage periods can produce a cleansing bath that removes calculus or tartar and stains together with the bulk of any bacterial infection yet has no harmful effects on the materials used in the manufacture of dental prostheses.

EXAMPLES

The invention is further illustrated by the following Examples in which parts and percentages are by weight of the total composition except where otherwise stated.

Example 1

Tartaric acid and a dense, granular form of anhydrous sodium carbonate of food grade containing less than 0.3% of chloride were separately dried on a Calmic (Trade Mark) fluid bed drier for 15 minutes at 80° C. Each product was found to have a free surface moisture content below 0.2%.

A portion of tartaric acid was premixed in a small shear/diffusive mixer with 0.032% of HEXACOL Indigo Carmine Supra dye, 0.082% of peppermint flavourant and 0.033% aniseed flavourant.

The premix was transferred to a tumble mixer and the balance of tartaric acid and the other components admixed to give a final composition for tabletting:

| | |
|---|---|
| "OXONE" (Trademark) | 57.72% |
| Tartaric acid (total) | 24.88% |
| Anhydrous Sodium Carbonate | 12.27% |
| CARBOWAX (Trademark) 6000 | 0.82% |
| Anhydrous Sodium perborate "Ground Mix" | 4.182% |
| Dyestuff (as above) | 0.032% |
| Total flavourant (as above) | 0.115% |

By weight of the "Ground Mix" the anhydrous sodium perborate "Ground Mix" consisted of 74.3% anhydrous sodium perborate ground together with 25.5% of anhydrous sodium carbonate and 0.2% NANSA S80 (Trade Mark) to an intimately mixed fine powder.

The final composition for tabletting was fed to a MANESTY D3 press and was straightforwardly formed into tablets of weight 3.0 g, diameter 22 mm and thickness 4 mm. Whilst the tablets were a little soft initially, they presented a good uniformly smooth surface with a blue mottled appearance.

On placing one tablet in 100 ml tap water at 30° C., dissolution was accompanied by vigorous effervescence and there was no trace of solids residue, within 50 seconds.

The pH of a clear 1% solution was determined and found to be 3.4. Using more than one aliquot of water the pH was found to vary about 3.6 by plus or minus 0.3. This variation was attributed to varying aliquot sizes and is acceptable experimental error.

The cleansing bath produced was tested for efficacy using naturally soiled dentures bearing stains and accumulations of calculus or tartar. Almost complete elimination of such accumulations occured with soaking for <15 minutes and stains were simultaneously removed. Before reapplication, the dentures required a simple rinsing under running water from the tap. No ulceration was suffered by denture wearers in the test period.

A tendency to restain to a greyish shade was noted in some denture wearers. This was overcome by including a proportion of disodium dihydrogen pyrophosphate as shown in Example 4.

Examples 2–6

The method of Example 1 was followed, where applicable substituting sodium bisulphate for the tartaric acid, using the following components:

|  | Ex. 2 | 3 | 4 | 5 | 6 |
|---|---|---|---|---|---|
| "OXONE" (contains KHSO$_4$.K$_2$SO$_4$.2KHSO$_5$) | 58.4 | 58.0 | 56.90 | 46.12 | 58.40 |
| Tartaric acid | — | 25.7 | 24.52 | — | 25.20 |
| Sodium bisulphate | 25.27 | — | — | 41.00 | — |
| Anhydrous sodium carbonate (chloride 0.3%) | 12.0 | 12.0 | 11.77 | 9.50 | 12.08 |
| Anhydrous sodium perborate "Ground Mix" | 4.196 | — | 4.05 | 3.28 | — |
| Disodium dihydrogen pyrophosphate | — | — | 2.64 | — | — |
| AVICEL PH101 (Trademark) | — | 4.196 | — | — | — |
| KELACID (Trademark) | — | — | — | — | 4.16 |
| HEXACOL INDIGO CARMINE SUPRA (Trademark) | 0.017 | 0.017 | 0.016 | 0.013 | 0.02 |
| Peppermint flavour | 0.084 | 0.084 | 0.078 | 0.063 | 0.1 |
| Aniseed flavour | 0.033 | 0.033 | 0.033 | 0.026 | 0.04 |

Where anhydrous sodium perborate "Ground Mix" is included, it is present as a disintegrant and has been replaced respectively by AVICEL PH100 (Trade Mark) and KELACID (Trade Mark) in Examples 3 and 6. The anhydrous sodium perborate "Ground Mix" may well act as an aid to tabletting; certain of the replacements are known aids to tabletting and to disintegration of the tablet.

Results

All these compositions were found to be effective in dissolving in water at 20° C. to 50° C. to a clear solution, of pH 3.4 to 4.0 that remove calculus or tartar accumulations. Additionally, a bacterial count before and after use of tablets according to Examples 1 and 4 in cleansing baths for dentures showed marked reduction after cleansing.

If more than one tablet is used to produce a clear solution then correspondingly more water is required.

These tablets, all containing the same dyestuff, produce an initially blue coloured cleansing bath which colour fades after about 2–8 minutes depending on the water bath temperature and the bleaching action of the monopotassium monopersulphate-containing triple salt.

Definitions

The term alkali metal cation as used in the specification is restricted to lithium, sodium and potassium cations.

The term "free surface moisture content" is used herein to define that part of the moisture in the composition available for reaction, e.g. with calcium carbide to form acetylene, and includes some capillary water and loose bound water. Such moisture content may conveniently be measured by the well known modified Karl-Fischer Test or the moisture evolution analyser of DuPont.

It has been found that unless the proper free surface moisture contents of the composition as defined in the appended claims is realised, the tablets produced may be defective, exhibiting star cracks in the surfaces and a tendency to "cap", i.e. laminate, during pressing.

By substantially "chloride-free" as used herein is meant that the carbonate contains no more than trace amounts of chloride as impurity. Larger concentrations of chloride would be released at least in part as chlorine during storage, thus imparing the quality of the tablets and reducing their oxidising power. Additionally, excessive residual chloride would be released in the denture cleansing bath producing malodour and objectionable taste when cleaned dentures are worn by some users.

When the present invention includes sodium carbonate such carbonate is preferably a dense and granular form of anhydrous sodium carbonate containing less than 0.3% w/w of chloride.

I claim:

1. An anhydrous denture cleansing composition suitable for tabletting, having a free surface moisture content of less than 0.5% for dissolution in water to form a denture cleansing bath, consisting essentially of 10% to 40% by weight of a permonosulphate of the formula M$^1$HSO$_5$ wherein M$^1$ is an alkali metal cation; a tartar removal component selected from the group consisting of succinic acid, malic acid, tartaric acid, citric acid, a bisulphate of the formula M$^2$HSO$_4$ wherein M$^2$ is an alkali metal cation, and mixtures thereof; and an amount of a substantially chloride-free anhydrous alkali metal carbonate of formula M$_2^3$CO$_3$ wherein M$^3$ is an alkali metal cation which amount is sufficient to develop an initial pH of ≦4.5 in the denture cleansing bath.

2. A composition according to claim 1 wherein the free surface moisture content of the composition is ≦0.2% by weight of the composition.

3. A composition according to claim 1 wherein m$^1$ is potassium, M$^2$ is potassium or sodium or mixtures thereof, and M$^3$ is sodium.

4. A composition according to claim 1 wherein the permonosulphate is present as the triple salt KHSO$_4$.K$_2$SO$_4$.2KHSO$_5$.

5. A composition according to claim 1 and wherein the tarter removal component consists essentially of an alkai metal bisulphate.

6. A composition according to claim 1 and wherein the tartar removal component constitutes up to 45% by weight of the composition.

7. A composition according to claim 1 and wherein the tartar removal component consists essentially of from 17% to 28% by weight of the composition.

8. A composition according to claim 1 and wherein the tartar removal component consists essentially of an alkali metal bisulphate, tartaric acid or mixtures thereof and constitutes from 2% to 40% of the composition.

9. A composition according to claim 1 and wherein at least part of the tartar removal component comprises tartaric acid and the chloride-free anhydrous alkali metal carbonate is present in a stoichiometrical amount to from with the tartaric acid sodium hydrogen tartrate when the composition is dissolved to form a denture cleansing bath.

10. A composition according to claim 1 including up to 50% by weight based on the alkali metal carbonate of an alkali metal bicarbonate.

11. A composition as claimed in claim 1 including an anti-restaining agent.

12. A composition as claimed in claim 11 in which the anti-restraining agent comprises sulphamic acid or an alkali metal phosphate.

13. A composition as claimed in claim 11 in which the anti-restaining agent comprises disodium dihydrogen pyrophosphate present at up to 10% by weight of the composition.

14. A composition according to claim 1 and including a minor amount of surfactant.

15. A composition according to claim 1 and including a disintegrant in an amount of about 2% to about 20% of the composition.

16. A composition according to claim 1 and including an amount of dehydrated sodium perborate monohydrate of about 2.5% to about 6% by weight of the composition.

17. A composition according to claim 1 and including an aid to tabletting in an amount of up to 0.2% by weight of the composition.

18. A process for the preparation of an anhydrous denture cleansing composition suitable for tabletting having a free surface moisture content of less than 0.5%, consisting essentially of 10% to 40% by weight of a permonosulphate of the formula $M^1HSO_5$ wherein $M^1$ is an alkali metal cation; a tartar removal component selected from the group consisting of succinic acid, malic acid, tartaric acid, citric acid, a bisulphate of the formula $M^2HSO_4$ wherein $M^2$ is an alkali metal cation, and mixtures thereof; and an amount of a substantially chloride-free anhydrous metal carbonate of formula $M^3_2CO_3$ wherein $M^3$ is an alkali metal cation which amount is sufficient to develop an initial pH of $\leq 4.5$ in the denture cleansing bath comprising the steps of pre-drying selected components of the composition separately and dry mixing the dried components with the other components to produce the denture cleansing composition.

19. A process according to claim 18 wherein the components are dried to a free surface moisture content of 0.02% to 0.5% by weight of the composition.

20. A process according to claim 18 wherein the selected components are the tartar removal component and the chloride-free anhydrous alkali metal carbonate.

21. A process according to claim 18 wherein the tartar removal component includes an alkali metal bisulphate and the selected components are dried to a free surface moisture content of $\leq 0.2\%$ by weight of the dried components respectively.

22. A process according to claim 18 wherein the drying step is conducted on a fluid bed drier at 80° C. for 15 minutes.

23. A process according to claim 18 including the additional step of tabletting the mixture.

* * * * *